(12) United States Patent
Hobbs

(10) Patent No.: US 9,709,563 B2
(45) Date of Patent: Jul. 18, 2017

(54) PASSIVATION OF SURFACES AFTER LIGAND COUPLING

(75) Inventor: Roderick Nicholas Hobbs, Holt (GB)

(73) Assignee: Agilent Technologies, Inc., Santa Clara, CA (US)

( * ) Notice: Subject to any disclaimer, the term of this patent is extended or adjusted under 35 U.S.C. 154(b) by 461 days.

(21) Appl. No.: 12/723,458

(22) Filed: Mar. 12, 2010

(65) Prior Publication Data

US 2010/0233734 A1 Sep. 16, 2010

(30) Foreign Application Priority Data

Mar. 16, 2009 (EP) .................................. 09003784

(51) Int. Cl.
*G01N 33/543* (2006.01)

(52) U.S. Cl.
CPC .............................. *G01N 33/54393* (2013.01)

(58) Field of Classification Search
CPC .................................................... G01N 33/543
See application file for complete search history.

(56) References Cited

U.S. PATENT DOCUMENTS

| | | | |
|---|---|---|---|
| 4,267,234 A | 5/1981 | Rembaum | |
| 4,358,388 A | 11/1982 | Daniel et al. | |
| 4,452,773 A | 6/1984 | Molday | |
| 4,454,234 A | 6/1984 | Czerlinski | |
| 4,530,956 A | 7/1985 | Ugelstad et al. | |
| 4,554,088 A | 11/1985 | Whitehead et al. | |
| 4,563,510 A | 1/1986 | Ugelstad | |
| 4,654,267 A | 3/1987 | Ugelstad et al. | |
| 4,672,070 A | 6/1987 | Takahashi et al. | |
| 4,695,392 A | 9/1987 | Whitehead et al. | |
| 4,695,393 A | 9/1987 | Chagnon et al. | |
| 4,783,336 A | 11/1988 | Margel et al. | |
| 4,795,698 A | 1/1989 | Owen et al. | |
| 4,816,567 A | 3/1989 | Cabilly et al. | |
| 4,964,007 A | 10/1990 | Satomi et al. | |
| 5,196,193 A * | 3/1993 | Carroll ....................... | 424/172.1 |
| 5,248,772 A * | 9/1993 | Siiman et al. ................ | 536/112 |
| 5,466,609 A | 11/1995 | Siiman et al. | |
| 5,576,220 A | 11/1996 | Hudson et al. | |
| 5,639,620 A | 6/1997 | Siiman et al. | |
| 5,707,877 A | 1/1998 | Siiman et al. | |
| 5,776,706 A | 7/1998 | Siiman et al. | |
| 5,891,468 A * | 4/1999 | Martin et al. ................. | 424/450 |
| 6,015,695 A | 1/2000 | Casterman et al. | |
| 6,231,982 B1 | 5/2001 | Wang | |
| 6,492,492 B1 * | 12/2002 | Stayton ........................ | 530/350 |
| 6,765,087 B1 | 7/2004 | Casterman et al. | |
| 6,855,329 B1 * | 2/2005 | Shakesheff et al. .......... | 424/409 |
| 7,169,618 B2 | 1/2007 | Skold | |
| 7,172,906 B2 | 2/2007 | Teng et al. | |
| 7,179,660 B1 | 2/2007 | Kirakossian et al. | |
| 7,214,640 B2 | 5/2007 | Margetts | |
| 7,378,035 B2 | 5/2008 | Margetts | |
| 2006/0115906 A1 | 6/2006 | Klapproth | |
| 2007/0251871 A1 * | 11/2007 | Tubbs et al. ................ | 210/198.2 |
| 2008/0103277 A1 * | 5/2008 | Campbell et al. .......... | 526/318.3 |

FOREIGN PATENT DOCUMENTS

| | | | |
|---|---|---|---|
| EP | 0140489 A | | 5/1985 |
| EP | 404097 | | 9/1996 |
| WO | 84/03358 A | | 8/1984 |
| WO | 84/03358 A2 | | 8/1984 |
| WO | 93/11161 | | 6/1993 |
| WO | WO 2006/078618 | * | 7/2006 |

OTHER PUBLICATIONS

Chica et al, Curr Opin Biotechnol 16(4):378-84, Aug. 2005.*
Witkowski et al, Biochemistry 38(36): 11643-50, Sep. 7, 1999.*
Seffernick et al, J Bacteriol 183 (8): 2405-10, Apr. 2001.*
Kumaran Ajikumar et al., Langmuir 23: 5670-5677, 2007.*
EP 09003784.7-1405, Official Communication Pursuant to Article 94(3) EPC, Jul. 3, 2013.

* cited by examiner

*Primary Examiner* — Phuong Huynh

(57) ABSTRACT

Passivated substrates are provided for use in assays, comprising at least one covalently bonded ligand having specific binding activity for a molecule, and at least one covalently bonded blocking agent, wherein said ligand is directly bonded to the substrate surface. In certain embodiments, the ligand and blocking agent are covalently bonded only to the substrate surface, and not directly bonded to each other. In certain other embodiments, the ligand and blocking agent have at least one additional covalent bond to one another. Methods for preparing and using passivated substrates in bioassays are also provided.

8 Claims, 4 Drawing Sheets

PASSIVATION OF SURFACES AFTER LIGAND COUPLING

CROSS REFERENCE TO RELATED APPLICATIONS

This patent application claims the benefit of European Patent Application No. 09003784.7 as filed on Mar. 16, 2009.

FIELD OF THE INVENTION

This invention relates generally to compositions and methods for isolation of cells and analytes.

BACKGROUND OF THE INVENTION

Particulate reagents are frequently used in bioassays. However, use of these reagents is often hampered by nonspecific binding of biological molecules to the particles, resulting in false positives, or apparent high background binding, leading to inaccurate detection and poor quantitation and purification. Numerous efforts have been made to reduce nonspecific binding, typically involving covalently attaching gelatin, dextrans or modified dextrans or the like to the particles to provide a hydrophilic layer to reduce nonspecific adsorption or binding of unwanted biological molecules to the particles. The nonspecific binding of biomolecules is reputed to be minimized by the dextran layer due to its essentially uncharged and hydrophilic character and the mobility of the attached dextran chains.

For example, U.S. Pat. Nos. 5,639,620 and 5,776,706 to Siiman purport to describe gelatin and aminodextran coated polymer core particles, including the preparation of aminodextrans having varying amounts of amine groups, and a method of crosslinking gelatin and aminodextran without the use of a stabilizer. The method is described as producing colloidal particles having a surface with hydrophilic properties. Siiman states that the polymer and antibody layers on the particles should be covalently bound to each other in order to reduce dissociation and conformational changes, and that this can be accomplished by preparing particles having a biodegradable coating to which can be attached pendent biological substances, such as monoclonal antibodies. Similarly, U.S. Pat. No. 5,707,877 to Siiman purports to describe discrete colloidal particles having a solid core coated with a first layer of a water soluble gelatin and a second layer of an aminodextran, said coating being crosslinked or fixed by the action of a chemical crosslinking agent and having a plurality of pendent functional groups. The pendent functional groups are described as having terminal aldehyde or carboxylate groups, amine groups, sulfhydryl groups or maleimidyl groups, and polyclonal or monoclonal antibodies, and the core is described as being metallic particles formed in gelatin solution or preformed particles which are then coated with the gelatin. Siiman further describes discrete colloidal particles having pendent biological functional groups such as polyclonal and monoclonal antibodies covalently attached to the crosslinked second aminodextran layer by means of a heterobifunctional crosslinking agent, which purportedly acts as a bridging group between the biological substance or functional group and the crosslinked gelatin or aminodextran. Siiman further describes a process for coating a solid core material which has a hydrophobic surface with first gelatin layer and a second aminodextran layer, crosslinking the adsorbed outer coating and derivatizing the crosslinked coating to obtain a product having a desired reactive species covalently bound to said crosslinked coating surface.

In addition, U.S. Pat. No. 5,466,609 to Siiman purports to describe colloidal particles having a core material and a gelatin/aminodextran coating, said coating being crosslinked or fixed by the action of a chemical crosslinking agent and having a plurality of pendent functional groups. Biological substances or molecules, especially monoclonal antibodies, allegedly may be covalently attached to the crosslinked second aminodextran layer by means of a heterobifunctional crosslinking agent so as to enable advantageous use of said antibody functionalized particles in biological separations and assays. The heterobifunctional crosslinking agent purportedly acts as a bridging group between the biological substance or functional group and the crosslinked gelatin or aminodextran. The monoclonal antibody containing particles are reported to be useful in a variety of positive and negative biological assays.

U.S. Pat. No. 6,231,982 to Wang describes the preparation of magnetic and non-magnetic particles coated with a polyaldehyde dextran material and a process for making the same. The particles are allegedly prepared by first oxidizing dextran with selected oxidizing agents to obtain a dextran-derived substance having a plurality of pendent aldehyde groups, and coupling the dextran-derived substance to a magnetic or non-magnetic particle having pendent amino groups or other functional groups reactive with aldehyde groups to obtain a dextran-coated particle. The polyaldehyde dextran coated particles are alleged to be suitable for use in immunological assays and exhibit a reduced matrix effect in such assays when compared to conventional particles lacking a polyaldehyde dextran coating.

U.S. Pat. No. 5,576,220 to Hudson describes methods and systems of unhindered construction and display of tethered organic ligand molecules, and more particularly to preparation and use of thin film, substantially non-crosslinked hydrophilic polar multifunctionalized polymers (HPMP) anchored to a variety of functionalized substrates so that the HPMP forms a thin film matrix layer providing a highly hydrated high dielectric environment equivalent to an aqueous solution, for affinity binding of ligands to target molecules. The HPMP thin film is allegedly 200-2000 Å thick, and reportedly can be any biocompatible substantially uncrosslinked high molecular weight highly soluble polysaccharide, such as high molecular weight dextrans. The ligands are allegedly singly tethered to the HPMP by a "permanent" strong covalent bond so that subsequent displacement of the target molecule does not also displace the ligand from the HPMP.

U.S. Pat. No. 5,248,772 to Siiman purports to describe the use of aminodextrans in the formation and coating of colloidal metal(O) particles, and the formation of colloidal metal dispersions using aminodextrans as reductants and protective agents. After crosslinking the aminodextran coating using a crosslinking agent, the coated particles reportedly can be used to covalently bind proteins.

U.S. Pat. No. 7,169,618 to Skold purports to describe a method for separating material using colloidal magnetizable aggregates optionally silanized and coated with polysaccharides having pendant functional groups to which is linked a member of a specific binding pair.

U.S. Pat. No. 7,172,906 to Teng purports to describe a method for reducing nonspecific binding in a binding assay for the determination of an analyte in a sample where one of the reagents for conducting the binding assay comprises a solid support comprising a polysaccharide. The method comprises including in an assay medium for conducting the binding assay a soluble compound comprising a protein linked to a polysaccharide.

U.S. Pat. No. 7,179,660 to Kirakossian purports to describe a polysaccharide coated carrier having a coating of at least two successive layers of polysaccharide, and a layering method for coating by employing sequential coating with oppositely charged polysaccharides. In certain embodiments, the pendent functional groups reportedly are used to bind specific binding partners to the surface coating of the carrier.

Accordingly, researchers have devised methods for attaching coatings to particles and for attaching ligands or members of binding pairs to the attached coatings on the particles. However, there remains a need for improved methods for preparing particles for diagnostic assays and the like having reduced nonspecific binding.

SUMMARY OF THE INVENTION

Passivated substrates are provided for use in assays, comprising at least one covalently bonded ligand having specific binding activity for a molecule, and at least one covalently bonded blocking agent, wherein said ligand is directly bonded to the substrate surface. In certain embodiments, the ligand and blocking agent are covalently bonded only to the substrate surface, and not directly bonded to each other. In certain other embodiments, the ligand and blocking agent have at least one additional covalent bond to one another.

Preferably, the blocking agent is a hydrophilic polymer, such as a polysaccharide, polypeptide or polyoxyethylene oxide, or the like. In certain embodiments, the polysaccharide is an aminosaccharide having a molecular weight of from 1 kDa to 500 kDa, more preferably from 3 kDa to 170 kDa, or more preferably from 10 kDa to 40 kDa.

The substrate is not particularly limited, and can be selected from particles, filters, fibers, glass slides, microtiter plates and microfluidic devices, and the like. The substrate typically comprises a glass, ferromagnetic material, or a suitable polymer selected from polystyrenes, acrylates, methacrylates, or combinations or composites thereof. The passivated substrate can further comprise an additional blocking agent.

In additional embodiments, there is provided a method for preparing a passivated substrate for use in bioassays comprising providing a substrate having reactive groups; covalently attaching a ligand to the substrate via the reactive groups; and further reacting at least one blocking agent to the substrate via the reactive groups, wherein the ligand is directly bonded to the substrate surface. In certain preferred embodiments, the reactive groups are selected from carboxyl, amine, hydrazide, aldehyde, sulfhydryl or maleimide moieties. In particular embodiments, the method further comprises reacting an additional blocking agent to the substrate via the reactive groups. In yet other embodiments, the method can further comprise subjecting the passivated substrate to a crosslinking reaction to crosslink the ligand to the blocking agent, in order to provide further stability to the ligand and prevent loss. Preferably, the blocking agent is a hydrophilic polymer, including but not limited to a polysaccharide, polypeptide or polyoxyethylene oxide, or the like. In particular embodiments, the polysaccharide is an aminosaccharide, preferably having a molecular weight of from 1 kDa to 500 kDa, more preferably from 3 kDa to 170 kDa, or more preferably from 10 kDa to 40 kDa. In certain embodiments, the blocking agent (e.g., a polysaccharide) comprises functional groups selected from amine, hydrazide, aldehyde, sulfhydryl or maleimide.

Preferably the substrate is in the form of a particle, filter, fiber, glass slide, microtiter plate or a microfluidic device. In certain preferred embodiments, the particle is a magnetic particle, preferably the magnetic particle is ferromagnetic.

In yet other embodiments, there is provided a method for passivating a magnetic particle, comprising providing a magnetic particle having reactive groups; covalently attaching a ligand to the magnetic particle via the reactive groups; and further reacting at least one blocking agent to the magnetic particle via the reactive groups.

In additional embodiments, there are provided methods for conducting bioassays with reduced nonspecific binding to a ligand bearing substrate comprising providing the passivated substrate; contacting the passivated substrate with a sample comprising a biological substance such that the biological substance binds to the ligand; and separating the passivated substrate from the sample.

In yet additional embodiments, there is provided the use of a passivated particle in bioassays, comprising providing a passivated particle comprising a covalently attached ligand having specific binding activity for a biomolecule and at least one blocking agent, wherein said ligand and blocking agent are directly bonded to the substrate surface; contacting the passivated particle with a sample comprising a biomolecule such that the ligand having specific binding activity for a biomolecule binds the biomolecule; and separating the passivated particle from the sample.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Figure 1:
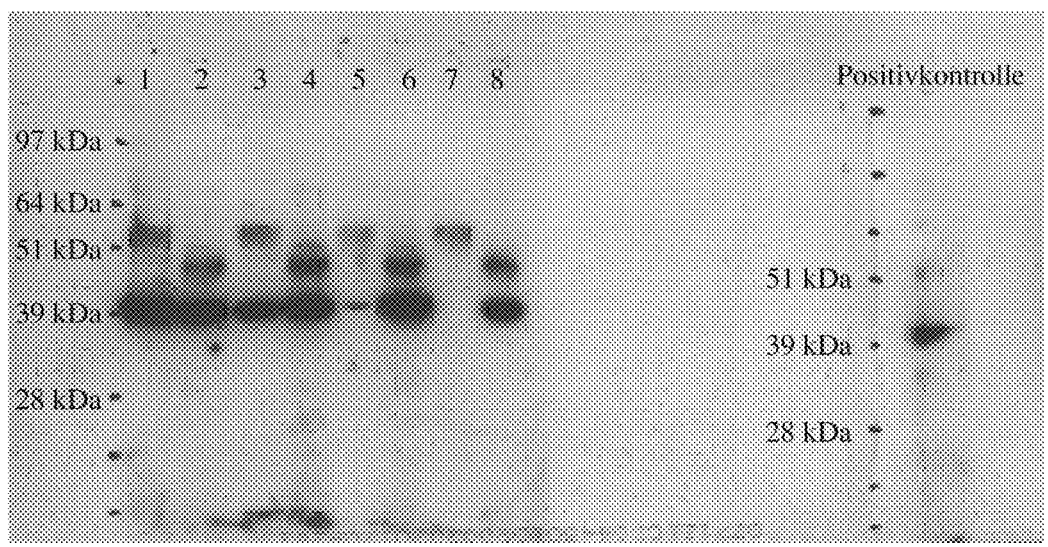
FIG. 1 illustrates the capture of GFP-$His_6$ fusion protein by anti-$(His)_6$Tag LodeStars™.

Before the present invention is described in detail, it is to be understood that unless otherwise indicated this invention is not limited to specific cell types, polysaccharides, ligands, or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "an analyte" includes two or more analytes; reference to "a ligand" includes two or more ligands, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the terms "ligand" and "targeting ligand" refer to a molecule having specific binding activity for a molecule, usually a biomolecule. A typical ligand is an antibody with specific binding for a particular protein or epitope.

As used herein the term "passivate" refers to a process whereby the surface of a particle is rendered relatively inert biologically. In particular, a passivated particle exhibits reduced nonspecific binding of biological molecules or cells to a surface.

The present invention provides novel compositions and methods for isolating and detecting molecules. The present inventors have surprisingly discovered improved methods for preparing passivated substrates, wherein targeting ligands are coupled directly to substrates such as solid phase reaction surfaces such as fibers, polymeric beads or particles, followed by coupling of blocking agents such as polysaccharides to reduce nonspecific binding. Although practitioners have been extensively employing related compositions and methods for sample preparation and the like, the present inventors are the first to discover that targeting ligands can be bonded to substrate surfaces with retention of activity and specific binding prior to covalent attachment of blocking agents to the substrate, an unexpected and surprising result. Further, the present inventors have discovered that passivation of surfaces employed in diagnostic assays results in the reduced nonspecific binding of molecules to surfaces, greatly improving assay precision and sensitivity, and may improve the assay signal to noise ratio sufficiently to make an assay useful that would otherwise not yield useful results.

Accordingly, passivated substrates are provided for use in assays, comprising at least one covalently bonded ligand having specific binding activity for a molecule, and at least one covalently bonded blocking agent, wherein said ligand is directly bonded to the substrate surface. In certain embodiments, the ligand and blocking agent are covalently bonded only to the substrate surface, and not directly bonded to each other. In certain other embodiments, the ligand and blocking agent have at least one additional covalent bond to one another.

In additional embodiments, there are provided methods for preparing a passivated substrate for use in bioassays comprising providing a substrate having reactive groups; covalently attaching a ligand to the substrate via the reactive groups; and further reacting at least one blocking agent to the substrate via the reactive groups, wherein the ligand is directly bonded to the substrate surface. In certain preferred embodiments, the reactive groups are selected from carboxyl, amine, hydrazide, aldehyde, sulfhydryl or maleimide moieties. In particular embodiments, the method further comprises reacting an additional blocking agent to the substrate via the reactive groups. In yet other embodiments, the method can further comprise subjecting the passivated substrate to a crosslinking reaction to crosslink the ligand to the blocking agent, in order to provide further stability to the ligand and prevent loss. Preferably, the blocking agent is a hydrophilic polymer, including but not limited to a polysaccharide, polypeptide or polyoxyethylene oxide, or the like. In particular embodiments, the polysaccharide is an aminosaccharide, preferably having a molecular weight of from 1 kDa to 500 kDa, more preferably from 3 kDa to 170 kDa, or more preferably from 10 kDa to 40 kDa. In certain embodiments, the blocking agent (e.g., a polysaccharide) comprises functional groups selected from amine, hydrazide, aldehyde, sulfhydryl or maleimide. Various aspects and embodiments of the invention will be described in greater detail below.

II. Compositions

The compositions of the invention include passivated substrates for use in assays, comprising at least one covalently bonded ligand having specific binding activity for a molecule, and at least one covalently bonded blocking agent, wherein said ligand is directly bonded to the substrate surface. In preferred embodiments, the ligand and blocking agent are not covalently bonded to one another. An additional blocking agent may be provided. In additional embodiments, the blocking agent can be crosslinked to itself, to an additional blocking agent, and/or to the ligand.

A. Ligands

"Ligands" or "targeting ligands" are molecules having specific binding activity for a molecule, more typically a biomolecule. There is no particular requirement for a ligand other than that it exhibit specific binding for a target molecule, i.e., having a high binding affinity of at least $10^6 M^{-1}$, and usually between about $10^6 M^{-1}$ and about $10^8 M^{-1}$.

Ligands can include antibodies, receptors, enzymes, lectins, synthetic or natural peptides, saccharides, oligonucleotides, biotin binding ligands such as avidin and streptavidin and recombinant versions thereof, immunoglobulin binding proteins from bacteria such as Protein A, Protein G and Protein L and recombinant versions thereof.

In one embodiment, a ligand is an antibody having specific binding for a particular protein or epitope. The term "antibody" is used in the broadest sense and specifically covers intact natural antibodies, monoclonal antibodies, polyclonal antibodies, multispecific antibodies (e.g. bispecific antibodies) formed from at least two intact antibodies, synthetic antibodies such as tetravalent antibodies, and antibody fragments, so long as they exhibit the desired biological activity. Human antibodies include antibodies made in nonhuman species. The term antibody also encompasses Ig molecules formed only from heavy chains, such as those obtained from Camelids, and described in U.S. Pat. Nos. 6,765,087 and 6,015,695 to Casterman, for example. The term antibody also encompasses fusion or chemical coupling (i.e., conjugation) of antibodies with additional agents useful for detection, isolation or diagnostic purposes (e.g., fluorophores or biotin). "Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata, et al. (1995) *Protein Eng.* 8(10), 1057-1062) single-chain antibody molecules; and multispecific antibodies formed from antibody fragments. The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567). "Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. The humanized antibody includes a PRIMATIZED™ antibody wherein the antigen-binding region of the antibody is derived from an antibody produced by immunizing macaque monkeys with the antigen of interest.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP404,097 and WO 93/11161.

However, the ligands utilized in the compositions and methods of the invention are not limited to antibodies. Additional proteinaceous ligands can be utilized, such as receptor proteins or portions thereof, such as soluble receptors. For example, proteinaceous ligands include, but are not limited to, lectins; peptide mimetics of pharmaceutical agents or antibody epitopes; cytokines, including interleukins, chemokines, and the like; cytokine receptors or fragments thereof; fusion proteins; recombinant soluble Fc receptors; immunoglobulin binding proteins from bacteria such as Protein A, Protein G and Protein L and recombinant versions thereof; biotin binding ligands such as avidin and streptavidin and recombinant versions of thereof.

Non-proteinaceous ligands can also be utilized, so long as the ligand exhibits specific binding for the desired target molecule to be isolated or detected in the assay. For example, nonproteinaceous ligands include, but are not limited to, hormones, oligosaccharides, oligonucleotides and nucleic acid analogues including peptide nucleic acid (PNA) and morpholino oligonucleotides, synthetic molecules, including those from chemical or peptide libraries, or pharmaceutical agents, and the like.

B. Blocking Agents

Blocking agents function to shield the substrate surface from sample constituents that exhibit nonspecific binding. Suitable blocking agents include hydrophilic polymers such as polysaccharides, synthetic oligosaccharides, proteins and synthetic peptides. In certain embodiments, the polymer has a mean molecular weight of from about 1 kDa to about 500 kDa, more preferably from about 3 kDa to about 170 kDa. In certain preferred embodiments, the polymer has a mean molecular weight from about 10 kDa to about 40 kDa. In general, lower molecular weight blocking agents will cause less steric hindrance for subsequent target molecule binding, though higher molecular weight polymers may more effectively shield the underlying surface. The optimum molecular weight of the blocking agent and number of functional groups can be determined experimentally.

In a preferred embodiment, the polymer is a polysaccharide and is a dextran of mean molecular weight of from about 1 kDa to about 500 kDa, more preferably from about 3 kDa to about 170 kDa. In certain preferred embodiments, the polysaccharide is from about 10 kDa to about 40 kDa.

In an additional embodiment, methyl-capped pegylation reagents can be employed, that on reaction with the ligand and aminodextran derivatized substrate attach polyethylene oxide (PEO) chains of 4-8 PEO units, though such reagents are not limited to these chain lengths. In addition, a wide range of protein modification and conjugation reagents are commercially available to further modify and covalently cross-link the surface to optimize the surface characteristics for a particular application.

In yet other embodiments, the blocking agent is a protein which does not participate in any binding reaction. Examples of blocking proteins include albumin, gelatin and casein, and the like.

C. Substrates

The substrate is not particularly limiting, and can be selected from particles, filters, glass fibers, glass slides, microtiter plates and microfluidic devices, and the like. Substrates can be formed from inorganic materials such as metal or metalloid oxides (e.g., silica, alumina, titania, zirconia, vanadia, zeolite, mullite, glass, etc.), ferromagnetic materials, or organic materials such as carbon fibers, cellulosic materials (e.g., nitrocellulose, cellulose acetate), synthetic polymers including poly(vinylchloride), polyacrylamide, polyacrylate, polyolefins (e.g., polyethylene, polypropylene, polytetrafluoroethylene (PTFE)), poly(4-methylbutene, polystyrene, polyurethanes, polyacrylonitriles, polymethacrylate, poly(ethylene terephthalate), polysiloxanes, nylon, poly(vinyl butyrate), and the like, or mixtures or composites of any of the above. Preferably, the passivated substrate comprises a natural or synthetic polymer such as but not limited to styrenic or (meth)acrylate based polymers, or glasses, ferromagnetic materials, modified silica, or combinations or composites thereof.

The compositions and methods of the invention can be practiced with a wide range of particles, both magnetic and nonmagnetic. The particle preferably comprises a polymeric matrix, further comprising functional groups that can be made to react with a ligand molecule. The particle surface may be hydrophobic in character or have a variety of hydrophilic groups prior to coupling the ligand and blocking agent. The activation chemistry and coupling conditions can be optimized to enable interaction of the ligand and blocking agent with the surface and subsequent covalent coupling.

In preferred embodiments, the particles are magnetic or superparamagnetic particles prepared as described in U.S. Pat. Nos. 7,214,640 and 7,378,035 to Margetts. These particles are available commercially under the tradename LodeStars™ particles (Varian, Inc., Palo Alto, Calif.). In a particularly preferred embodiment, the superparamagnetic particle is LodeStars™ 2.7 Carboxyl, nominally 2.7 μm in diameter, and with a microcrystalline ferric oxide component dispersed uniformly throughout the particle. The ferric oxide provides the particles with their superparamagnetic properties, causing them to move rapidly in an applied magnetic field. Also, because no permanent magnetism is retained, they can be fully redispersed once the field is removed. The particle surface is covered with carboxylic acid groups to which ligands can be covalently coupled using well-established chemistries such as carbodiimide chemistry. The particles can be loaded with ligands containing amine groups at suitable concentrations (e.g., 10 μg protein/mg particle). The particles can be then employed as a solid phase in manual and automated assays, and following covalent coupling of specific affinity ligands, can be employed to isolate targets in biological samples including cells, proteins and other biomolecules.

Additional magnetic particles that can be utilized include those comprising a core-and-shell beads with a magnetic core and a hard shell coating of polymerized monomer or a silanizing agent, as described in U.S. Pat. No. 4,267,234 to Rembaum (polyglutaraldehyde shell around ferrofluid core particles); U.S. Pat. No. 4,454,234 to Czerlinski (suspension or emulsion polymerized coating around submicron magnetic particles); U.S. Pat. Nos. 4,554,088, 4,695,392 and 4,695,393 to Whitehead et al. (silanized magnetic oxide particles of polydisperse size and shape); U.S. Pat. No. 4,672,040 to Josephson (polysilane coated magnetic particles); U.S. Pat. No. 4,783,336 to Margel et al. (suspension polymerized polyacrolein around ferrofluid particles); U.S. Pat. No. 4,795,698 to Owen et al. (bovine serum albumin coating); and U.S. Pat. No. 4,964,007 to Yudelson (gelatingum arabic-surfactant coating); those comprising a core-and-shell beads with a magnetic core and a loose shell of random coil or globular polymer which may or may not be crosslinked, as described in U.S. Pat. No. 4,452,773 to Molday (dextran coating around ferrofluid particles) and U.S. Pat. No. 4,795,698 to Owen et al. (protein such as bovine serum albumin around ferrofluid particles; those comprising magnetic latex materials formed by uniformly embedding ferrofluid particles in polystyrene latex particles, as described in U.S. Pat. No. 4,358,388 to Daniel et al.; and those comprising porous polymer particles filled with magnetic materials such as polymer-ferrite or polymer maghemite composite systems, as described in U.S. Pat. Nos. 4,563,510, 4,530,956 and 4,654,267.

Other nonlimiting substrates that can be used include silica particles, glass slides, glass fibers, microtiter plates and microfluidic devices.

III. Methods for Preparing Passivated Substrates

The invention further provides methods for preparing passivated substrates. One skilled in the art will recognize that the devices and methods of the present invention can be implemented in various fashions to provide substrates which minimize nonspecific binding of compounds.

Accordingly, there are provided methods for preparing passivated substrates for use in bioassays comprising: providing a substrate having reactive groups, covalently attaching a ligand to the substrate via the reactive groups, and further reacting at least one blocking agent to the substrate via the reactive groups, wherein the ligand and blocking agent are covalently bound directly to the substrate. In particular embodiments, the ligand and blocking agent are not covalently bound to one another. The methods can further comprise reacting an additional blocking agent to the substrate via the reactive groups.

In one embodiment, the reactive groups on the substrate surface are preferably relatively stable under the ligand coupling conditions so that sufficient reactive sites survive to be available for coupling with the blocking agent. Exemplary reactive groups include N-hydroxysuccinimide and N-hydroxysulfosuccinimide esters. These reactive esters are sufficiently stable under the conditions employed to provide for reaction of both ligand and blocking agent with the substrate surface. In addition, these esters provide the option of removing the ligand prior to addition of the blocking agent or reacting the substrate with addition blocking agents, as the reactive esters should survive throughout the time required for ligand coupling, optional substrate washing, and reaction with blocking agent.

In particular preferred embodiments, the substrate is a magnetic particle such as LodeStars™ 2.7 Carboxyl. Covalent coupling of proteins (e.g., antibodies) to LodeStars™ 2.7 Carboxyl can, employ activation of the carboxylic acid groups using a carbodiimide to form reactive O-acylisourea moieties. Subsequent reaction of this moiety with an amine on the protein forms a covalent amide bond with the protein. Though this approach can be successful for antibody coupling, the O-acylisourea is relatively unstable and can undergo side reactions. An alternative approach is the use of carbodiimides to form N-hydroxysuccinimide esters or N-hydroxysulfosuccinimide esters. These reactive esters form a stable amide bond on reaction with an amine on the antibody.

Activation of LodeStars™ 2.7 Carboxyl with EDC and NHS can be performed in a wide variety of reaction conditions. In exemplary methods, the LodeStars™ can be reacted at pH 5 or pH 6 (e.g., using 25 mM MES), however, the ligand and blocking agent coupling can be performed at these pH's or at a higher pH in amine-free buffers. The protocol below is therefore illustrative, and optimization should be performed for a particular application:

1. Dispense LodeStars™ 2.7 Carboxyl (500 μl, approx $1.5 \times 10^9$ particles) into a 10 ml tube. 2. Centrifuge the tube briefly to bring the LodeStars™ to the bottom and collect the particles to the side by placing the tube next to a magnet. Completely aspirate the supernatant using micropipette. Similarly perform 2 times 1.0 ml washes with 0.01M NaOH for 10 minutes on a bottle roller to leave the LodeStars™ as a pellet following the final wash. 3. Similarly perform 3 times 1.0 ml washes with deionised water, leaving the LodeStars™ as a pellet following the final wash. 4. Add 500 μl of a freshly prepared 50 mg/ml solution of N-hydroxysuccinimide in cold 25 mM MES, pH 6.0, and vortex mix. 5. Prepare a 50 mg/ml solution of EDC in cold 25 mM MES, pH 6.0, and immediately add 500 μl of this solution to the LodeStars™ suspension and vortex mix. 6. Place the LodeStars™ on a bottle roller and allow the activation to proceed for 30 minutes. 7. Centrifuge briefly and apply the tube to a magnet and completely aspirate the supernatant. 8. Similarly, quickly perform 2 times 10 ml washes with cold 25 mM MES, pH 5.0, using vortexing to resuspend the LodeStars™ and magnetic separation each time to leave them as a pellet. 9. Add 600 μl of 25 mM MES, pH 5.0, followed by 600 μl of a 1 mg/ml solution of protein in the same buffer and vortex, and allow the coupling to proceed by mixing on a bottle roller for 3 hours at room temperature. 10. Apply the tube to the magnet and aspirate the supernatant. Add 10 ml of 100 mM Tris-HCl, pH 7.4. Vortex briefly and mix on a bottle roller for 1 hour to block any remaining reactive sites.

11. Transfer the LodeStars™ to a buffer appropriate to their application.

In a preferred embodiment, the formation of NHS and Sulfo-NHS esters on the surface of the LodeStars™ provides amine-reactive sites that are relatively stable under some pH conditions. It is postulated that this relative stability enables survival of sufficient reactive sites for coupling of the blocking agent following coupling of the ligand.

One skilled in the art will readily appreciate the range of substrates, ligands and blocking agents that can be utilized. For example, nonparticulate substrates such as glass slides, polymeric substrates and glass fibers can utilized, as described in greater detail in Example 6.

IV. Applications and Methods of Use

In certain embodiments, methods are provided for conducting bioassays with reduced nonspecific binding to a ligand bearing substrate, comprising providing a passivated substrate; contacting the passivated substrate with a sample comprising a biological substance such that the biological substance binds to the ligand; and separating the passivated substrate from the sample. In yet additional embodiments, there is provided the use of a passivated particle in bioassays, comprising providing a passivated particle comprising a covalently attached ligand having specific binding activity for a biomolecule and at least one blocking agent, wherein said ligand and blocking agent are directly bonded to the substrate surface; contacting the passivated particle with a sample comprising a biomolecule such that the ligand having specific binding activity for a biomolecule binds the biomolecule; and separating the passivated particle from the sample. In certain preferred embodiments, the passivated substrate is a magnetic particle. These methods and uses are exemplified in the Examples below, which demonstrate that cells and other biological target molecules can be separated from a complex mixture with reduced nonspecific binding using the passivated substrates provided herein.

V. Advantages of the Invention

The passivated substrates and methods for preparing them provide unexpected convenience and cost savings. Some of the advantages of the substrates and methods include the following:

Passivation of the surface immediately follows ligand coupling and does not require additional activation steps to prepare the surface for reaction with the blocking agent.

A range of highly purified blocking agents such as aminodextrans and modified dextrans of various molecular weights are commercially available or can readily be prepared by those skilled in the art.

Blocking agents such as aminodextrans and modified dextrans provide a hydrophilic non-toxic layer for cells.

Blocking agents such as aminodextrans and modified dextrans enable gentle release of captured cells.

Blocking agents such as aminodextrans and modified dextrans provide sites for further modification to optimize surface characteristics or provide cross-linking if required.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric. All solvents were purchased as HPLC grade, and all reactions were routinely conducted in the air unless otherwise indicated.

Abbreviations:
Amdex Aminodextran
His Histidine
IgG Immunoglobulin G
SDS Sodium dodecyl sulfate
MES 4-morpholineethanesulfonic acid
EDC N-(3-dimethylaminopropyl)-N'-ethylcarbodiimide hydrochloride
PBS phosphate buffered saline
DMSO dimethylsulfoxide
SDS-PAGE SDS Polyacrylamide gel electrophoresis
DST disuccinimidyl tartrate
GAM Goat anti-mouse IgG
RAM Rat anti-mouse IgG
SAM Sheep anti-mouse IgG
MES 4-morpholineethanesulfonic acid
NHS N-hydroxysuccinimide
Sulfo-NHS N-hydroxysulfosuccinimide
PEO and PEG poly(ethylene oxide)
rProtein G recombinant Protein G

EXAMPLE 1

Isolation of a Polyhistidine-Tagged Fusion Protein Using Anti-(His)$_6$-Tag Monoclonal Antibody-Coated Magnetic Particles Genetically engineered polyhistidine tagged proteins are commonly employed in a wide variety of research applications. Their purification and detection usually takes advantage of the interaction of the polyhistidine sequence with certain heavy metal chelates. As an alternative, we coupled a mouse IgG$_1$ anti-(His)$_6$-Tag monoclonal antibody to 2.7 μm diameter superparamagnetic particles (LodeStars™ 2.7 Carboxyl, Varian, Inc., Palo Alto, Calif.) and subsequently coupled aminodextrans of a wide range of mean molecular weight to passivate the surface. The method of preparation of the anti-(His)$_6$-TagLodeStars™ is described below.

Ligand coupling was performed as follows: A 100 mg aliquot of LodeStars™ 2.7 Carboxyl was dispensed into a 10 ml polypropylene tube, a magnet was applied to the tube to isolate the magnetic particles, and the supernatant was aspirated. Two 10 ml washes with 0.01M NaOH were performed by adding the solution, replacing the cap, vortexing and placing on a bottle roller for 10 minutes each time. The magnetic particles were centrifuged for a few seconds, a magnet was applied to isolate the particles again, and the supernatant was removed by aspiration. Three 10 ml washes with 18 MΩ water were similarly performed and the resulting washed pellet of magnetic particles was cooled to 4° C. A 3 ml aliquot of a 50 mg/ml solution of Sulfo-NHS in cold 25 mM MES pH 5.0 was added to the pellet and vortexed, followed by the addition of a freshly prepared 50 mg/ml solution of EDC in cold 25 mM MES pH 5.0 (3 ml) and vortexing the magnetic particle suspension. Activation was allowed to proceed for 30 minutes with mixing using a bottle roller. The magnetic particle suspension was centrifuged for a few seconds, applied to a magnet and the supernatant aspirated. Two 10 ml washes with cold 0.1M sodium phosphate, 0.15M NaCl, pH 7.2 were performed using the magnet and aspiration to remove the supernatant as described previously and the LodeStars™ were resuspended by vortexing in 5 ml PBS pH 7.4. Aliquots (1.25 ml) of the activated LodeStars™ suspension were added immediately to 1.15 ml volumes of the anti-(His)$_6$-Tagmonoclonal (685 μg/ml) in cold PBS pH 7.4, vortexed briefly, placed between coolbags at 4° C. in a plastic bottle and mixed on a bottle roller for 1 hour to allow coupling. The suspension was centrifuged for a few seconds and then applied to a magnet and the supernatant aspirated.

Passivation with dextran was performed as follows: Two 10 ml washes of the LodeStars™ with cold 0.1M MES pH 5.0 were performed using the magnet and aspiration to remove the supernatant each time and the LodeStars™ were resuspended by vortexing in 5 ml 25 mM MES pH 5.0 containing 10 mg/ml aminodextran of mean molecular weight 10 kD, 40 kD or 170 kD having respectively an average of 3.2, 9.3 and 66 amines per molecule. To the fourth sample 1.5 ml of a 10 mg/ml 3 kD aminodextran in cold 25 mM MES pH 5.0 was added. Coupling was allowed to proceed for 2 hours with mixing, as described for reaction with anti-(His)$_6$-Tag monoclonal above. To all of the preparations, 500 µl of a cold 10 mg/ml solution of glucosamine-HCl in 25 mM MES pH 5.0 was added and mixed for 1 hour as described above to remove any remaining reactive sites. The ligand-coupled LodeStars™ were stored in a fridge overnight.

Further passivation with PEG was optionally performed as follows: The preparations were applied to a magnet and supernatants were aspirated. Each anti-(His)$_6$-Tag/dextran magnetic particle preparation was washed with three 10 ml aliquots of 1% (w/v) Tween 20, PBS pH 7.4, 0.1% (w/v) sodium azide, then 10 ml PBS pH 7.4, 0.1% (w/v) sodium azide and 10 ml 18 MΩ water. Each preparation was transferred to a 5 ml calibrated polypropylene tube, using more water to ensure maximum transfer of the LodeStars™. A 4.5 ml PBS pH 7.4, 0.1% (w/v) sodium azide wash was performed on each preparation and resuspended in 2.5 ml of this buffer to yield a nominal 10 mg/ml LodeStars™ concentration. Half of each suspension (1.25 ml) was transferred to a 10 ml polypropylene tube for pegylation. The LodeStars™ suspensions were applied to a magnet and the supernatants aspirated. For each preparation, two 10 ml washes with PBS pH 7.4 were performed followed by a 10 ml wash with 0.1M sodium phosphate, 0.15M NaCl, pH 7.2. Each preparation was resuspended in 1.25 ml of this buffer. NHS-m-dPEG (100 mg, Quanta BioDesign, Ltd) was dissolved in 1.0 ml DMSO and 25 µl of this solution added to each 1.25 ml LodeStars™ suspension and mixed on a bottle roller for 2 hours to allow pegylation of the antibody and remaining amines on the aminodextran. The NHS-m-dPEG conjugation results in the addition of a polyethylene oxide chain having eight ethylene oxide subunits in length with a terminal methoxy group, attached via an amide linkage to the primary amines. The preparations were applied to a magnet and supernatants aspirated. Each preparation was washed twice with PBS pH 7.4, 0.1% (w/v) sodium azide and then resuspended in 10 ml of this buffer to yield a nominal 1.25 mg/ml suspension.

The pegylated and non-pegylated anti-(His)$_6$-Tag/dextran LodeStars™ were assayed for His$_6$-Tag binding using a short synthetic fluorescein-labeled peptide having the sequence Fluorescein-GGGHHHHHH (M942 peptide). Particles derivatized with aminodextran and PEG or Tris alone were used as controls. Results are shown in Table 1.

TABLE 1

Peptide binding to anti-(His)$_6$-Tag/dextran LodeStars, with and without pegylation

| Particle preparation | M942 peptide bound to particles (pmole/mg) |
|---|---|
| anti-(His)$_6$-Tag 3 kD aminodextran | 6.15 |
| anti-(His)$_6$-Tag 10 kD aminodextran | 8.70 |
| anti-(His)$_6$-Tag 40 kD aminodextran | 7.05 |
| anti-(His)$_6$-Tag 170 kD aminodextran | 8.55 |

TABLE 1-continued

Peptide binding to anti-(His)$_6$-Tag/dextran LodeStars, with and without pegylation

| Particle preparation | M942 peptide bound to particles (pmole/mg) |
|---|---|
| anti-(His)$_6$-Tag 3 kD aminodextran pegylated | 11.55 |
| anti-(His)$_6$-Tag 10 kD aminodextran pegylated | 11.70 |
| anti-(His)$_6$-Tag 40 kD aminodextran pegylated | 11.70 |
| anti-(His)$_6$-Tag 170 kD aminodextran pegylated | 10.35 |
| control 3 kD aminodextran pegylated | 0.6 |
| control 10 kD aminodextran pegylated | 0.45 |
| control 40 kD aminodextran pegylated | 0.75 |
| control 170 kD aminodextran pegylated | 0.6 |
| control Tris-blocked | 3.3 |

Coupling of aminodextran to the control magnetic particles resulted in a substantial reduction of non-specific binding of the small peptide to the anti-(His)$_6$-Tag ligand. This difference is shown by comparing the value 3.3 pmole/mg obtained for the control Tris-blocked LodeStars™ and the other control (no antibody) LodeStars™ having various molecular weight aminodextrans coupled. Binding of M942 to anti-(His)$_6$-Tag LodeStars™ is not particularly dependent on the molecular weight of the coupled aminodextran, presumably because of the peptide's small size.

It is apparent from the results shown in Example 1 (Table 1) that there is a significant difference in binding capacity for M942 between the pegylated and non-pegylated anti-(His)$_6$-Tag LodeStars™. Pegylation increases M942 binding, possibly because pegylation prevents any nonspecific interactions of the covalently bound antibody with other structures on the LodeStars™ surface. The antibody might therefore be in a more favorable conformation for antigen binding.

EXAMPLE 2

Use of Anti-(His)$_6$-Tag Coated Particles to Purify GFP-His$_6$ Fusion Protein

The effect of dextran and PEG coating on the ability of anti-(His)$_6$-Tag LodeStars™ to isolate full length His$_6$-Tag proteins was tested. The test protein was a His$_6$-Tag fusion protein: green fluorescent protein (GFP-His$_6$ fusion protein) of 43 kD expressed in HeLa cells. The purification methodology is summarized below. Five 10 cm-Plates (each about 6×10$^5$ cells) were transfected using SuperFect® (Qiagen GmbH) as per manufacturers instruction. The transfection was checked after two days. About 30% of the cells were transfected. All cells were pooled and lysed in 5 ml lysis buffer; 500 µl were used in each subsequent experiment.

Preparation: HeLa cells expressing a 43 kD His$_6$-Tag green fluorescent protein (GFP-His$_6$ fusion protein) were washed in PBS pH 7.4 and resuspended in lysis buffer (20 mM HEPES/KOH pH 7.4, 125 mM NaCl, 0.5 mM EDTA, 1% Igepal, 10% Glycerol, EDTA-free Protease-Inhibitor), the cells were incubated on ice for 30 minutes, homogenized by ultrasonic treatment and cell debris was removed by centrifugation.

Sample Incubation: aliquots of 20 µl (200 µg) anti-(His)$_6$-Tag labeled magnetic particles (prepared as described in Example 1) were washed twice with PBS pH 7.4 and then with lysis buffer. The HeLa cell lysate was incubated with the anti-(His)$_6$-Tag LodeStars™ for 1.5 h at 4° C., followed by washing the labeled LodeStars™ with lysis buffer three times and resuspending them in SDS-sample buffer (250 mM Tris pH 6.8, 8% SDS, 40% Glycerin, 20% Mercaptoethanol, 0.008% Bromphenol blue), heating to 95° C. for 5 minutes, and removing debris by centrifugation. The supernatant was subjected to SDS-PAGE; the results are shown in FIG. 1 ("Capture of GFP-His$_6$ fusion protein by anti-(His)$_6$-Tag LodeStars™.") Lane 1: anti-(His)$_6$-Tag 3 kDa aminodextran; Lane 2: anti-(His)$_6$-Tag 3 kDa aminodextran PEG; Lane 3: anti-(His)$_6$-Tag 10 kDa aminodextran; Lane 4: anti-(His)$_6$-Tag 10 kDa aminodextran PEG; Lane 5: anti-(His)$_6$-Tag 40 kDa aminodextran; Lane 6: anti-(His)$_6$-Tag 40 kDa aminodextran PEG; Lane 7: anti-(His)$_6$-Tag 170 kDa aminodextran; Lane 8: anti-(His)$_6$-Tag 170 kDa aminodextran PEG. A sample of the 43 kD GFP-His6 fusion protein is shown in lane as a positive control. The band near 51 kD is the heavy chain of the antibody. Ideally, no antibody should be elutable from the LodeStars™, though as is well known to those skilled in the art, achieving complete covalent coupling of ligand to an activated surface is difficult. In the absence of pegylation, there is a dramatic reduction of GFP-His$_6$ fusion protein capture (43 kD band) with increasing molecular weight of aminodextran (see particularly lanes 5 and 7), indicating that the higher molecular weight dextran may interfere sterically with binding of the antibody to the fusion protein. Pegylation of the anti-(His)$_6$-Tag LodeStars™ largely negates this effect, resulting in greater binding of the GFP-His$_6$ fusion protein than observed in the absence of pegylation. Consistent with the results shown in Example 1, the magnetic particles derivatized with both dextran and PEG resulted in greater capture of target protein. In this example, the further modification of the surface with a pegylation reagent has also resulted in nonspecific binding of an additional protein component ~45-50 kD.

EXAMPLE 3

Use of Antibody Coated Particles to Bind Mouse Anti-CD34+ Antibody

The ability of labeled particles to isolate cells was investigated. Sheep anti-mouse IgG antibody (SAM) or rat anti-mouse IgG monoclonal antibody (RAM) coated magnetic particles (LodeStars™ 2.7 Carboxyl, Varian, Inc.) were prepared for isolation of CD34+ cells from human blood and their subsequent release. The covalently coupled SAM or RAM antibody binds an IgG1 mouse monoclonal antibody that in turn binds the CD34 cell surface antigen. In initial experiments, SAM or RAM antibody was covalently coupled to magnetic particles, followed by reacting with Tris to block remaining reactive esters.

Briefly, LodeStars™ 2.7 Carboxyl were activated using standard EDC/Sulfo-NHS chemistry in 25 mM MES pH 5.0 buffer to form reactive Sulfo-NHS esters as described in Example 1. SAM at 62.5, 125, 250, 500 and 1000 µg/ml or RAM at 1000 µg/ml were coupled in 25 mM MES pH 5.0 (SAM) or pH 6.0 (RAM), a magnet was applied to the suspension to collect the particles and the supernatant was aspirated. Following antibody coupling, remaining Sulfo-NHS esters were reacted with 0.1M Tris-HCl, pH 7.4 for 1 hour.

Binding of SAM or RAM coated LodeStars™ to mouse IgG1 anti-CD34 monoclonal antibody: Aliquots of SAM and RAM LodeStars™ (14.1 mg) in PBS pH 7.4, 0.1% (w/v) sodium azide were dispensed into 1.5 ml plastic tubes, applied to a magnet and the supernatants aspirated. A single 1% (w/v) Tween 20 PBS pH 7.4 0.1% (w/v) sodium azide wash (1 ml) was performed, followed by a wash in this buffer (1 ml) having a 0.1% (w/v) Tween 20 concentration. Anti-CD34 monoclonal antibody (1 ml, 200 µg) was added to the washed LodeStars™ pellet and binding was allowed to proceed with mixing on a bottle roller for 1 hour at room temperature. Following LodeStars™ separation on a magnet, the supernatants were aspirated and two 1.5 ml washes with the 0.1% (w/v) Tween 20 buffer were performed.

The antibody coupled LodeStars™ (blocked using Tris) were effective at binding a mouse IgG1 anti-CD34 monoclonal antibody. The RAM and SAM coupled to the LodeStars™ were assayed by amino acid analysis using standard methods. Bound mouse anti-CD34 was determined by difference in amino acid content between anti-CD34 loaded and non-loaded RAM and SAM LodeStars™. The amounts of SAM, RAM and the anti-CD34 monoclonal antibody on the LodeStars™ are shown in Table 2. It can be seen that increasing the concentration of SAM yields larger amounts of SAM coupled to the LodeStars™. However, it can be seen that the capacity to bind the monoclonal anti-CD34 is greatest using a SAM concentration of 500 µg/ml. This might be due to 'crowding' of the SAM on the LodeStars™ surface, therefore interfering with anti-CD34 binding.

TABLE 2

Amounts of SAM, RAM and anti-CD34 antibody on LodeStars

| Coupling concentration | Amino acids recovered (µg/mg LodeStars) | |
| --- | --- | --- |
| (µg/ml) | SAM or RAM | Anti-CD34 |
| SAM | | |
| 62.5 | 0.89 | 0.21 |
| 125 | 1.77 | 0.22 |
| 250 | 3.19 | 0.31 |
| 500 | 4.73 | 0.67 |
| 1000 | 7.48 | 0.56 |
| RAM | | |
| 1000 | 0.27 | 0.28 |

Capture of CD34+ cells by derivatized LodeStars™: As shown in Table 2, these SAM or RAM derivatized LodeStars™ were very effective for binding anti-CD34 antibody and hence target CD34+ cells. However, when a soluble CD34 peptide (PR34-peptide) was added to displace CD34 from the antibody, no release of cells from the particles occurred. It was postulated that failure to release the cells was due to non-specific interaction of the cells with structures other than the anti-CD34 antibody on the particles.

In a further experiment, antibody coupling was performed at pH 7.4 essentially as described above in Example 1. Magnetic particles (LodeStars™ 2.7 Carboxyl) were activated using standard EDC/Sulfo-NHS chemistry as described above, using SAM and RAM solutions at 2.0 mg/ml. Bovine serum albumin (BSA) or aminodextrans of mean molecular weight 3 kD, 10 kD, 40 kD and 170 kD (all at 10 mg/ml in 25 mM MES pH 5.0 buffer) were employed to block reactive sites following antibody coupling. The resulting derivatized particles were split into two batches, and one batch was further derivatized with PEG as previously described.

A fluorimetric assay was used to determine the binding capacity of the SAM and RAM coupled LodeStars™ for an Oregon Green 488-mouse IgG conjugate. In duplicate 1.5 ml tubes, 1 mg aliquots of LodeStars™ were added and each aliquot washed three times with 1 ml 0.1% (w/v) BSA, 0.1%

(w/v) Tween 20, PBS pH 7.4, 0.05% (w/v) NaN$_3$ by vortexing each time, applying to a magnet and aspirating the supernatant. To the washed LodeStars™, 1 ml of a 50 µg/ml conjugate solution in the buffer were added and mixed for 1 hour wrapped in aluminium foil to protect from light. Following aspiration of the supernatant, three 1 ml washes with the buffer were performed as described above. The LodeStars™ were resuspended in 1.5 ml aliquots of 0.1M NaOH, 0.1% (w/v) SDS for 15 minutes to elute bound conjugate and the fluorescence in the supernatant measured against standard amounts of the conjugate.

Figure 2:
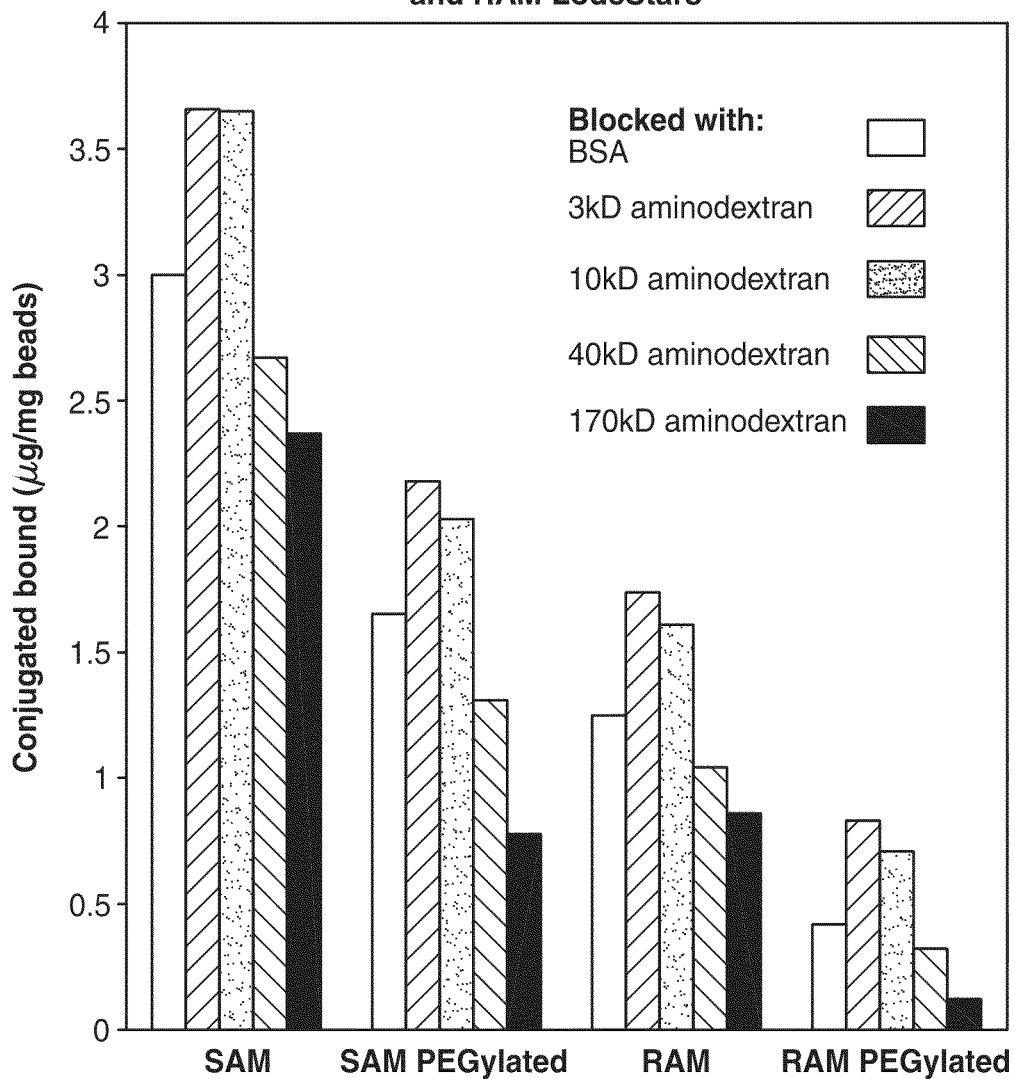
FIG. 2 illustrates the Oregon Green 488-mouse IgG conjugate binding capacity of albumin or aminodextran blocked SAM and RAM Lodestars™.

Results: the binding capacity of the SAM and RAM coupled LodeStars™ for an Oregon Green 488-mouse IgG conjugate was decreased with increasing molecular weight of aminodextran and pegylation, presumably due to steric hindrance (see FIG. 2). Albumin blocking of remaining reactive sites yielded LodeStars™ having conjugate binding capacity intermediate between the 10 kD and 40 kD aminodextrans. Additional pegylation reduced conjugate binding capacity in all cases.

EXAMPLE 4

Use of Antibody Coated Particles to Isolate CD34+ Cells

The aminodextran and/or PEG or albumin/PEG derivatized SAM and RAM magnetic particles (described in Example 3) were tested to determine the ability of the particles to isolate CD34+ cells (KG1A cells). Results of four KG1A cell isolation and release experiments using the aminodextran treated SAM and RAM LodeStars™ are shown in Table 3. It is clear that the LodeStars™ were effective at capturing and subsequently allowing release of KG1A cells on addition of the competing PR34 peptide which mimics the epitope on the CD34 antigen. The best performing particles captured and released a similar proportion of cells compared to experiments when the Dynal® products (SAM 450 and RAM 450, Invitrogen Dynal® AS, Oslo, Norway) were employed. These products are commonly employed in cell isolation procedures and well known to those skilled in the art. SAM and RAM derivatized particles prepared with 170 kD aminodextran exhibited reduced cell capture capacity, presumably due to steric hindrance inhibiting either anti-CD34 monoclonal binding activity or subsequent cell binding to this monoclonal. Also, the lower molecular weight aminodextrans (3 kD and 10 kD) allowed less cell release than the 40 kD and 170 kD aminodextrans, possibly because the 3 kD and 10 kD species failed to fully mask the surface.

BSA was quite effective at enabling cell release, but was less so following pegylation, an observation that is similar to that seen with the 170 kD aminodextran, which like BSA, has many primary amines as sites for pegylation.

TABLE 3

Cell capture and release using antibody coated LodeStars

| Experiment Number | Test Particles | Capture (%) With anti-CD34 antibody | Capture (%) Without antibody | Released Cells (% original cell population) With PR34-peptide | Released Cells (% original cell population) With wash buffer |
|---|---|---|---|---|---|
| 1 | SAM M450 | 94 | 19 | 78 | 5 |
|  | SAM BSA PEG | 94 | 20 | 27 | 3 |
|  | SAM 3 kD Amdex | 93 | 29 | 28 | 3 |
|  | SAM 10 kD Amdex PEG | 92 | 26 | 24 | 3 |
| 2 | SAM M450 | 94 | 15 | 74 | 10 |
|  | SAM BSA | 96 | 14 | 49 | 4 |
|  | SAM 40 kD Amdex PEG | 91 | 9 | 62 | 10 |
|  | SAM 170 kD Amdex PEG | 76 | 12 | 59 | 10 |
| 3 | SAM M450 | 89 | −9 | 68 | 7 |
|  | SAM 10 kD Amdex | 90 | −7 | 35 | 8 |
|  | SAM 40 kD Amdex | 87 | −1 | 57 | 6 |
|  | SAM 170 kD Amdex | 73 | −2 | 77 | 8 |
| 4 | RAM M450 | 91 | 17 | 30 | 10 |
|  | RAM 10 kD Amdex | 88 | −4 | 28 | 10 |
|  | RAM 40 kD Amdex | 85 | 17 | 61 | 17 |
|  | RAM 170 kD Amdex | 60 | 22 | 43 | 28 |

In conclusion, the aminodextran derivatization of the SAM and RAM coupled magnetic particles resulted in decreased nonspecific binding of the CD34+ cells. The method of derivatizing particles enabled specific capture of KG1A cells and their subsequent gentle release.

EXAMPLE 5

Effect of Modification of the Antibody/Aminodextran Layer on Stability and Non-Specific Binding Characteristics Chemical modification of the antibody/aminodextran layer alters both the stability of the layer to elution from the particles and its non-specific protein binding characteristics. A 40 ml volume of affinity-purified goat anti-mouse IgG (GAM) at 630 µg/ml was employed to covalently couple this antibody to 400 mg LodeStars™ 2.7 Carboxyl after activation by EDC/Sulfo-NHS, as described in Example 1. The GAM was coupled for 1 hour at 4° C. with mixing in 25 mM MES, 0.15M NaCl pH 5.0 before isolating the particles using a magnet and aspirating the supernatant. After antibody coupling, a 10 mg/ml solution (20 ml) of 40 kD aminodextran in cold 25 mM MES pH 5.0 was added after aspiration of the GAM and allowed to couple to the LodeStars™ for 2 hours at 4° C., followed by addition of 2 ml of 10 mg/ml 3 kD aminodextran in the same buffer and mixing as before for further 1 hour. Finally a 2 ml aliquot of 10 mg/ml glucosamine-HCl in the same buffer was added and mixed for a further 1 hour, and the LodeStars™ placed in a refrigerator overnight. Extensive washes of the resulting LodeStars™ were performed in PBS pH 7.4, 0.1% (w/v) sodium azide.

The LodeStars™ were split into several aliquots and modified further in the following ways: pegylated with Methyl-PEO4-NHS ester (Pierce product 22341) or Methyl-PEO8-NHS ester (Pierce product 22509) which couple short PEO chains to amines on the GAM and aminodextran; cross-linked with disuccinimidyl tartrate ((DST), Pierce Chemical Co., product 20589); or cross-linked with EDC in either 0.1M MES pH 5.0 or 0.1M MOPS, 0.9% (w/v) NaCl, pH 6.9. In both of the latter cases, 1 mg EDC was employed per mg LodeStars™ and the reaction was allowed to proceed for 1 hour at room temperature with mixing. To assess the stability of the GAM/aminodextran derivatized LodeStars™, 1 mg aliquots of the LodeStars™ were exposed to either 100 µl CelLytic™ MT Mammalian Tissue/Lysis reagent (Sigma) or this reagent containing 300 µg/ml cytoplasmic human kidney protein (Sigma product T-6445) for 1 hour at 4° C. Following extensive washing with the CelLytic™ reagent, the LodeStars™ were exposed to NuPAGE® LDS sample buffer (Invitrogen product NP0007) for 2 hours at room temperature and the supernatants aspirated.

Figure 3:
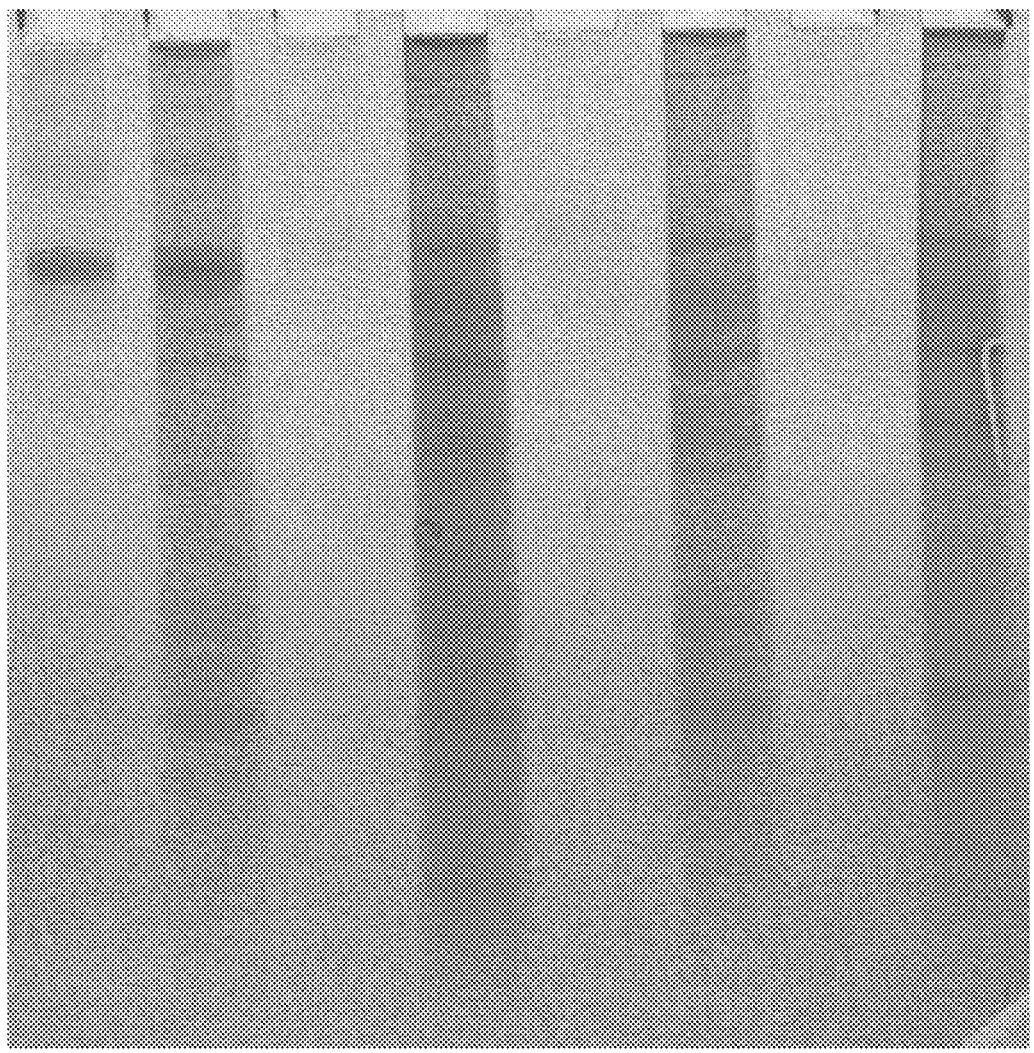
FIG. 3 shows a SDS-PAGE gel demonstrating the stability and nonspecific binding of modified LodeStars™.
Figure 4:
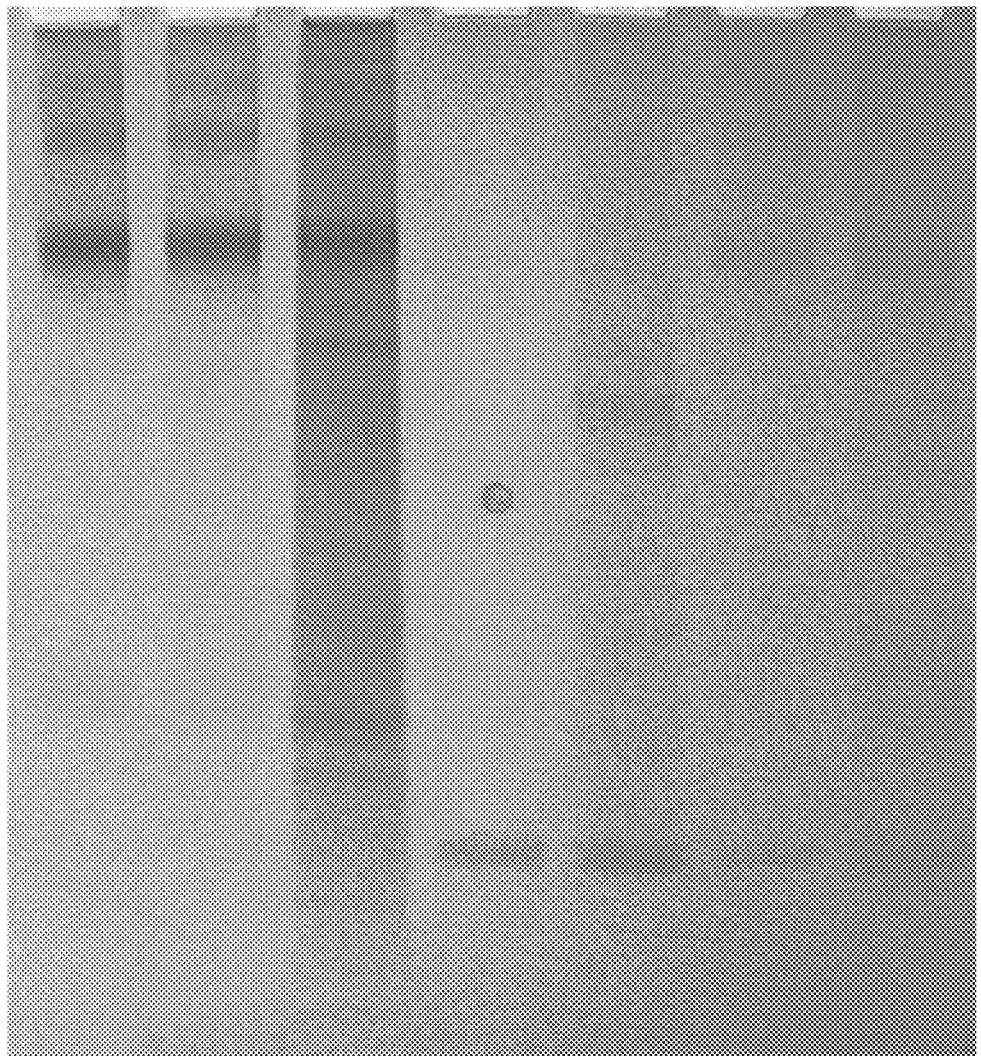
FIG. 4 shows a SDS-PAGE gel demonstrating the stability and nonspecific binding of modified LodeStars™.

The supernatants were run under non-reducing conditions on a 4-12% Bis-Tris SDS PAGE gel (Invitrogen product NP0321BOX) and silver stained with SilverQuest silver staining kit (Invitrogen product LC6070). The results are shown in FIGS. 3 and 4. FIG. 3 lane assignments: Lane 1: unmodified, Lane 2: unmodified+kidney protein, Lane 3: PEO4 modified, Lane 4: PEO4 modified+kidney protein, Lane 5: PEO8 modified, Lane 6: PEO8 modified+kidney protein, Lane 7: DST cross-linked, Lane 8: DST cross-linked+kidney protein. FIG. 4 lane assignments: Lane 1: unmodified, Lane 2: unmodified (separate batch), Lane 3: unmodified+kidney protein, Lane 4: EDC cross-linked at pH 5.0, Lane 5: EDC cross-linked at pH 5.0+kidney protein, Lane 6: EDC cross-linked at pH 6.9, Lane 7: EDC cross-linked at pH 6.9+kidney protein.

It can seen that without further modification of the GAM/aminodextran coated LodeStars™, a significant amount of GAM was elutable (FIG. 3, lane 1 and FIG. 4, lanes 1 and 2). Pegylation and DST cross-linking considerably reduced the amount of GAM that was eluted (FIG. 3, lanes 3, 5 and 7).

FIG. 4 shows that EDC cross-linking considerably reduced the elution of the GAM (compare lanes 4 and 6 with lanes 1 and 2), particularly when the cross-linking was performed at pH 5.0. At this pH the rate of formation of the O-acylurea intermediate is more rapid, but so is its hydrolysis. Non-specific protein binding to EDC cross-linked GAM/aminodextran LodeStars™ was also much reduced when compared to those that were unmodified (compare FIG. 4, lanes 5 and 7 with lane 3). More protein bound to LodeStars™ that were cross-linked at pH 5.0 than at pH 6.9 and it is surmised that this was due to a reaction which results in the formation of an N-acylurea on the surface at pH 5.0 that is essentially absent at pH 6.9.

EXAMPLE 6 rProtein G Coated Polyacrylic Acid Functionalized Glass Fiber Silica

Pieces of polyacrylic acid functionalized glass fiber silica approximately 35 mm×10 mm were added to six 50 ml polypropylene tubes and each was washed three times with 50 ml of 18 MΩ water, followed by a 50 ml wash of 25 mM MES pH 5.0 to leave the material as a moist pad. Activation of carboxylic acid groups on the surface was performed by adding 2.0 ml of a 50 mg/ml solution of N-hydroxysulfosuccinimide in 25 mM MES pH 5.0, followed by 2.0 ml of a 50 mg/ml solution of EDC in 25 mM MES pH 5.0. Activation was allowed to proceed for 30 minutes with mixing on a bottle roller.

The polyacrylic acid functionalized glass fiber silica pieces were each washed three times with 50 ml cold 25 mM MES pH 4.55, and to three pieces of activated material was added 2.0 ml of a 0.4 mg/ml solution of rProtein G in 25 mM MES pH 4.55. To the remaining three pieces, 2.0 ml of this buffer only was added to act as controls. rProtein G coupling was allowed to proceed for 1 hour at 4° C. with mixing on a bottle roller.

Aliquots (2.0 ml) of 1 mg/ml solutions of either 40 kD aminodextran or 10 kD aminodextran in 25 mM MES pH 4.55 or 25 mM MES pH 4.55 buffer only were each added to one piece of rProtein G coated material and one piece of control material and mixed for a further 2 hours at 4° C. on a bottle roller.

Remaining reactive sites were eliminated by addition of 2.0 ml aliquots of 50 mM Tris-HCl pH 7.4 to all samples of material and mixed for a further 1 hour. The supernatants were aspirated and four washes with 18 MΩ water performed and the materials freeze-dried overnight.

Binding of an Oregon Green 488-mouse IgG conjugate to the pieces was assayed as follows. Two approximately 5 mm square pieces from each piece were carefully cut and weighed into 1.5 ml NoStick tubes. Each piece was washed three times with 1 ml of 0.9% (w/v) fish skin gelatin, 0.1% (w/v) Tween 20, PBS pH 7.4, 0.05% (w/v) sodium azide, vortexing the sample each time in the buffer.

One ml of a 50 µg/ml solution of the conjugate in this buffer added to each sample. The tubes were wrapped in foil and mixed for 1 hour on a bottle roller. Supernatants were aspirated and each piece of material washed three times with 1 ml of the buffer, vortexing the sample each time to ensure efficient washing. Aliquots of 0.1M NaOH, 0.1% (w/v) SDS (1.5 ml) were added to each tube, then wrapped in foil and mixed on a bottle roller for 10 minutes to elute the conjugate.

Conjugate in the supernatants was assayed fluorimetrically and the amounts of conjugate per mg dry weight of material was calculated. The results are shown in Table 4. It can be seen that increasing the molecular weight of the blocking aminodextran from 10 kD to 40 kD results in reduced binding of the mouse IgG conjugate, presumably due to steric hindrance.

TABLE 4

Oregon Green 488-mouse IgG conjugate binding to control and rProtein G coated glass fiber silica after passivation with aminodextran

| Material | Amount (mg) | Conjugate bound µg per mg |
|---|---|---|
| Control Tris | 5.3 | 0.07 |
|  | 5.8 | 0.04 |
| Control 10 kD aminodextran | 4.0 | 0.06 |
|  | 5.2 | 0.05 |
| Control 40 kD aminodextran | 4.7 | 0.14 |
|  | 5.0 | 0.03 |
| rProtein G Tris | 4.9 | 0.26 |
|  | 4.9 | 0.28 |
| rProtein G 10 kD aminodextran | 4.9 | 0.28 |
|  | 5.2 | 0.28 |
| rProtein G 40 kD aminodextran | 4.4 | 0.18 |
|  | 4.4 | 0.22 |

This experiment demonstrates that ligands can be covalently bonded to substrates such as glass fibers followed by bonding of a blocking agent to reduce nonspecific binding.

What is claimed is:
1. A passivated substrate for use in assays, comprising
at least one covalently bonded ligand having specific binding activity for a molecule, wherein the covalently bonded ligand is directly bonded to a substrate; and at least one covalently bonded blocking agent, wherein the blocking agent is a hydrophilic polymer directly bonded to the substrate; and, further the blocking agent and the ligand have at least one additional covalent bond to one another.

2. The passivated substrate of claim 1, wherein the hydrophilic polymer is a polysaccharide, polypeptide or polyoxyethylene oxide.

3. The passivated substrate of claim 2, wherein the polysaccharide is an aminosaccharide having a molecular weight of from 1 kDa to 500 kDa.

4. The passivated substrate of any of claims 1, 2-3, wherein the substrate is selected from a particle, a filter, a fiber, a glass slide, a microtiter plate and a microfluidic device.

5. The passivated substrate of claim 4, wherein the substrate comprises a glass, a ferromagnetic material, or a polymer selected from a polystyrene, an acrylate, a methacrylate, or a combination or composite thereof.

6. The passivated substrate of claim 1, wherein the ligand is a biopolymer selected from the group consisting of an antibody, a diabody, a receptor, an enzyme, a lectin, a peptide, a natural peptide, a saccharide, an oligonucleotide, a biotin binding ligand, and an immunoglobulin binding protein.

7. The passivated substrate of claim 6, wherein the ligand has a binding affinity of at least $10^6$ $M^{-1}$ for the molecule.

8. The passivated substrate of claim 3, wherein the polysaccharide is an aminosaccharide having a molecular weight of from 10 kDa to 40 kDa.

* * * * *

UNITED STATES PATENT AND TRADEMARK OFFICE
CERTIFICATE OF CORRECTION

Page 1 of 1

PATENT NO. : 9,709,563 B2
APPLICATION NO. : 12/723458
DATED : July 18, 2017
INVENTOR(S) : Roderick Nicholas Hobbs It is certified that error appears in the above-identified patent and that said Letters Patent is hereby corrected as shown below:

In the Specification

In Column 4, Line 42, delete "Lodestars™." and insert -- LodeStars™. --, therefor.

In Column 12, Line 37, delete "TagLodeStars™" and insert -- Tag LodeStars™ --, therefor.

In Column 15, Line 14, delete "GFP-His6" and insert -- GFP-His$_6$ --, therefor.

In the Claims

In Column 21, Line 12, in Claim 4, delete "1, 2-3," and insert -- 1-3, --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*